United States Patent [19]
Rastatter et al.

[11] Patent Number: 5,961,443
[45] Date of Patent: Oct. 5, 1999

[54] THERAPEUTIC DEVICE TO AMELIORATE STUTTERING

[75] Inventors: Michael Pierre Rastatter; Joseph Stanley Kalinowski; Andrew Michael Stuart, all of Greenville, N.C.

[73] Assignee: East Carolina University, Greenville, N.C.

[21] Appl. No.: 08/831,043

[22] Filed: Apr. 1, 1997

Related U.S. Application Data

[60] Provisional application No. 60/022,839, Jul. 31, 1996.

[51] Int. Cl.$^6$ ..................................................... A61F 5/58
[52] U.S. Cl. ............................................. 600/23; 600/24
[58] Field of Search ........................... 128/846, 864–868; 600/23, 24, 27, 28

[56] References Cited

U.S. PATENT DOCUMENTS

| | | | |
|---|---|---|---|
| 3,349,179 | 10/1967 | Klein | 600/23 |
| 4,421,488 | 12/1983 | Parlenvi et al. | 434/185 |
| 4,464,419 | 8/1984 | Vildgrube et al. | |
| 4,662,847 | 5/1987 | Blum | 434/185 |
| 4,685,448 | 8/1987 | Shames et al. | |
| 4,727,582 | 2/1988 | de Vries et al. | |
| 4,784,115 | 11/1988 | Webster | 600/24 |
| 5,133,016 | 7/1992 | Clark | |
| 5,438,625 | 8/1995 | Klippel | |
| 5,478,304 | 12/1995 | Webster | 600/23 |
| 5,481,615 | 1/1996 | Eatwell et al. | |
| 5,647,834 | 7/1997 | Ron | 600/23 |
| 5,794,203 | 8/1998 | Kehoe et al. | 704/271 |

OTHER PUBLICATIONS

C. Pickett, "Stopping Stuttering," *The Daily Reflector* (Apr. 4, 1996, Section D, p. 1).

A. Stuart & J. Kalinowski, "Fluent Speech, Fast Articulatory Rate, and Delayed Auditory Feedback: Creating a Crisis for a Scientific Revolution?," *Perceptual and Motor Skills* 82, 211–218 (1996).

J. MacLeod, et al., "Effect of Single and Combined Altered Auditory Feedback on Stuttering Frequency at Two Speech Rates," *J. Commun. Disord.* 28, 217–228 (1995).

S. Hargrave, et al., "Effect of Frequency–Altered Feedback on Stuttering Frequency at Normal and Fast Speech Rates," *J. Speech. Hearing. Res* 37, 1313–1319,(1994).

J. Kalinowski, et al., "Effects of Alterations in Auditory Feedback and Speech Rate on Stuttering Frequency," *Language and Speech* 36(1), 1–16 (1993).

Catalog Edition, Casa Futura Technologies, Boulder, CO, Mar. 31, 1997.

*Primary Examiner*—Michael A. Brown
*Attorney, Agent, or Firm*—Myers Bigel Sibley & Sajovec, P.A.

[57] ABSTRACT

A device and method for ameliorating stuttering by providing an altered auditory feedback by employing a compact device configured for positioning in or adjacent the ear canal of an individual. The portable, self-contained device can be used on a "chronic" basis and includes a receiver for receiving auditory signals, an auditory delay and or frequency shift circuit, and a transmitter for transmitting the altered signal to the individual user.

54 Claims, 4 Drawing Sheets

THERAPEUTIC DEVICE TO AMELIORATE STUTTERING

RELATED APPLICATIONS

This application claims the benefit of U.S. application Ser. No. 60/022,839 filed on Jul. 31, 1996.

FIELD OF THE INVENTION

The present invention relates to devices or techniques which treat stuttering, and more particularly to devices employing altered auditory feedback to treat stuttering.

BACKGROUND OF THE INVENTION

In stutterers it is hypothesized that both the left and right hemispheres of the brain compete to send signals to the muscles that produce speech. This causes conflict and interruptions in a stutterer's speech flow pattern. In contrast, under this hypothesis, in non-stutterers no such competition exists and brain signals produce speech only from one side of the brain (typically the left), thereby producing fluent speech patterns. At least one report submits that stuttering is caused by interrelated sensory and motor deficits. See e.g. J. Kalinowski et al., *Effects Of Alterations In Auditory Feedback and Speech Rate On Stuttering Frequency*, 36(1) Language and Speech, p. 1–16 (1993).

Conventionally, stuttering has been treated by several different types of treatment including psychiatric therapy, drug therapy, and electrical signals such as altered auditory feedback. Two types of altered auditory feedback which have been studied include delayed auditory feedback ("DAF") and introduction of a masking noise or masked auditory feedback ("MAF"). Generally described, DAF imposes a delay on the delivery of a feedback speech signal to a speaker/stutterer, while MAF serves to compete with a speaker's auditory feedback. It has been known for some time that DAF methods can be used to treat stuttering. See e.g. R. Pollock et al., *A Solid State Delayed Auditory Feedback System*, Biomedical Engineering, December 1976, pp. 413–414.

For example, M. E. Wingate in *Stuttering: theory and treatment*, p. 237 (Irvington 1976), describes a type of altered auditory feedback which can include DAF (delayed auditory feedback) to provide an emphasis on phonation, i.e., slowing down to extend syllable duration. However, this type of auditory feedback is thought to be achievable with or without the use of DAF as long as the same technique of syllable prolongation was employed. See e.g. W. H. Perkins, *From Psychoanalysis to Discoordination*, in H. H. Gregory (Ed.) *Controversies about stuttering therapy*, pp. 97–127 (University Press 1979). See also Andrew Stuart et al., *Fluent Speech, Fast Articulatory Rate, and Delayed Auditory Feedback: Creating a Crisis For A Scientific Revolution?*, 82 Perceptual and Motor Skills, p. 211–218 (1996).

In the past, slowed speech rates were found to be an important factor in the reduction of stuttering. For example, in W. H. Perkins et al., *Phone rate and the effective planning time hypothesis of stuttering*, 29 Jnl. of Speech and Hearing Research 747–755 (1979), the authors reported that stuttering was virtually eliminated when speakers reduced speech by approximately 75%.

U.S. Pat. No. 4,685,448 to Shames et al. discloses a vocal tactile feedback apparatus to improve stuttering by providing delayed auditory feedback in the form of mechanical vibrations. The device consists of a control mechanism suitable for inserting into a pocket, a separate microphone, and an electromechanical transducer attached to the neck of the user to provide the delayed feedback.

U.S. Pat. No. 4,464,119 to Vildgrube et al. discloses a device for correcting speech using DAF. The device is composed of a separate microphone, an analog control circuit, and an earphone. Similarly, Chinese Patent No. CN 1087742 to Ren, Zhiqiang, entitled, *The Method of Delaying Analog Signals and The Stammer Curing Instrument Using This Method*, proposes a DAF treatment device employing a plurality of storage mediums such as a recording magnetic head and a reading magnetic head.

Other treatment for stuttering continues to be uncertain, with many of the devices and therapies demanding excessive time in speech laboratories with specialized therapists and equipment or which treat stuttering by slowing down speech to make the speech sound more fluent. Conventional DAF treatment has utilized devices that are relatively large and stationary and not suited for prolonged use. In addition, drug therapies also have proven to be of somewhat limited efficacy and can potentially result in undesired side effects.

OBJECTS AND SUMMARY OF THE INVENTION

The present invention, recognizing that DAF treatment can be effectively employed on a chronic use basis, and that such chronic use therapy can act to cure stuttering or reduce the number of stuttering events, provides as a first object of the present invention a safe, portable, and effective apparatus for ameliorating stuttering by allowing the use of the device during infancy, adolescence, or adult life.

It is another object of the present invention to provide a compact, self-contained and economical device which is small enough to be insertable into or adjacent an ear and which can reduce stuttering to provide more normal fluent speech flow at a more normal speed.

It is yet another object of the invention to provide for a device that allows treatment of stuttering by ongoing use of the device, in addition to merely clinically provided episodic treatments.

These objects, advantages and other features are provided by the present invention which as a first aspect includes a portable ameliorative stuttering device which is supported in the ear of an individual. The device includes a housing having opposing distal and proximal surfaces. Part of the housing, including at least the proximal surface, is configured for positioning within the ear canal of the individual. The device also includes a wave signal processor contained within the housing. The wave signal processor comprises a receiver which generates an input signal responsive to an auditory signal associated with the individual's speech. The wave signal processor also includes a delayed auditory feedback circuit operably associated with the receiver which generates a delayed auditory signal. A transmitter contained within the housing is operably associated with the delayed auditory feedback circuit for transmitting the delayed auditory signal to the individual. The device also includes a power source operatively associated with the wave signal processor for supplying power thereto.

An additional embodiment of the device is a behind the ear ameliorative stuttering device. In this embodiment the device includes an ear mold having a portion adapted to be received into the individual's ear. The device includes a housing in communication with the ear mold and configured for positioning behind the ear of the individual. The housing contains a receiver which generates an input signal responsive to an auditory signal associated with speech of the individual. The device also includes a delayed auditory feedback circuit disposed in the housing and operatively associated with the receiver. The circuit generates a delayed auditory signal. A transmitter operably associated with the delayed auditory feedback circuit transmits the delayed auditory signal to the ear canal of the individual. The device also includes a power source operatively associated with the receiver, the delayed auditory feedback circuit, and the transmitter for supplying power thereto.

Advantageously, the compact, portable device of the present invention now enables treatment of stuttering on a chronic or on-going basis. Additionally and advantageously, the device employs a microphone which is affixed to the ear. This is especially important in devices directed to users who are young. Beneficially, enabling and allowing day to day use in early childhood may provide a higher cure rate, or at least partial reduction, of stuttering at an earlier age. This type of device permits on-going therapy and feedback which is in complete contrast to conventional episodic type treatment (for example, therapy provided to a patient by a speech therapist with dedicated equipment at a clinic).

Yet another aspect of the present invention is a method for chronic amelioration of stuttering. The method comprises first positioning a self-contained ameliorative stuttering device for receiving auditory signals associated with the individual's speech in close proximity to the ear, the device adapted to be in communication with the ear canal of the individual. An audio signal associated with the individual's speech is received by the device. A delayed auditory signal responsive to the received audio signal is generated. The delayed auditory signal is then transmitted to the ear canal of the individual. Optionally, the method can also include comparing (a) a series of digitized voice samples input to the delay circuit, the voice samples corresponding to the speech of the individual, to (b) the output from the delay circuit to determine if the output delay is sufficient. Based on this comparison, the method can also advantageously include adjusting the time delay of the delayed auditory signal so as to be responsive to the determination of the comparing step, thereby increasing or decreasing the time delay output from the delay circuit corresponding to the number of stuttering events detected.

The foregoing and other objects and aspects of the present invention are explained in detail in the specification set forth below.

DETAILED DESCRIPTION OF PREFERRED EMBODIMENTS

The present invention will now be described more fully hereinafter with reference to the accompanying figures in which preferred embodiments of the invention are shown. This invention may, however, be embodied in many different forms and should not be construed as limited to the embodiments set forth herein. Like numbers refer to like elements throughout.

In the description of the present invention that follows, certain terms are employed to refer to the positional relationship of certain structures relative to other structures. As used herein, the term "distal" refers to a location in the direction away from the ear canal, while the term "proximal" refers to a location in the direction of the ear canal.

Generally described, the portable, compact device of the present invention includes a small housing configured for positioning behind the ear, or substantially in or within the ear canal; e.g., behind-the-ear ("BTE"), in-the-ear ("ITE"), and completely-in-the-canal ("CIC"). As will be discussed in more detail below, the ameliorative stuttering device includes a proximately positioned housing which preferably contains a wave signal processor including a receiver, a delayed auditory feedback circuit, and a transmitter therein. Certain components, such as a receiver or transducer, may be located away from the ear canal, although still within close proximity thereto. In operation, the portable ameliorative stuttering device receives input sound signals from a patient at a position in close proximity to the ear (such as via a microphone in or adjacent the ear), processes the signal, amplifies the signal, and delivers the processed signal into the ear canal.

Figure 1:
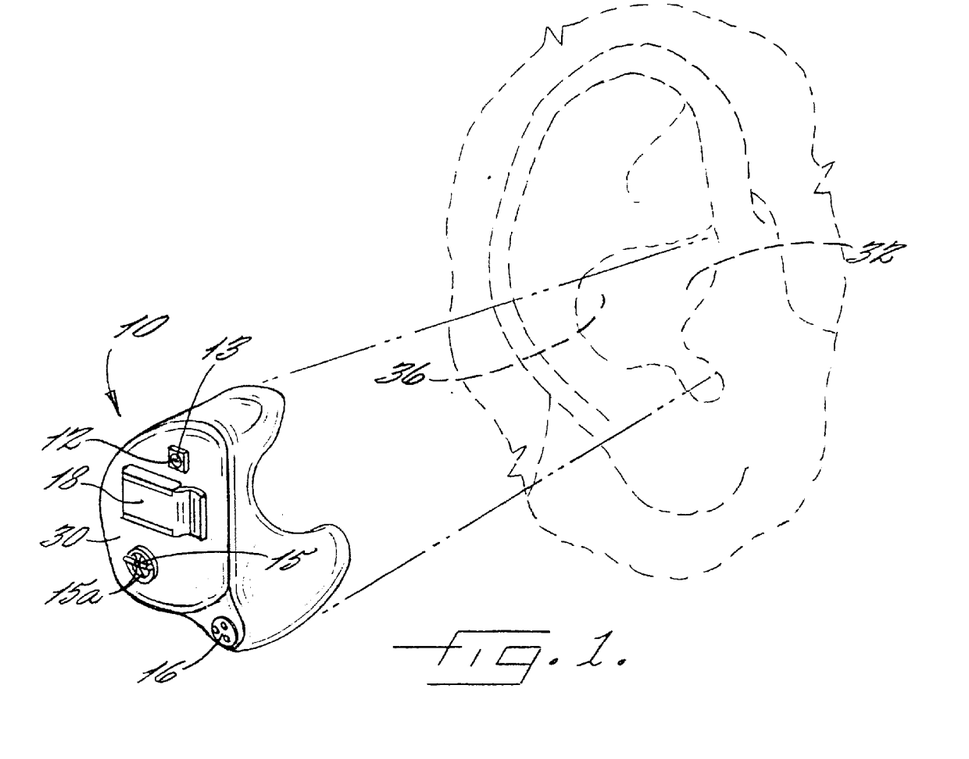
FIG. 1 is a side perspective view of a device for ameliorating stuttering positioned to be inserted in the ear canal ("ITE") in accordance with the present invention.
Figure 2:
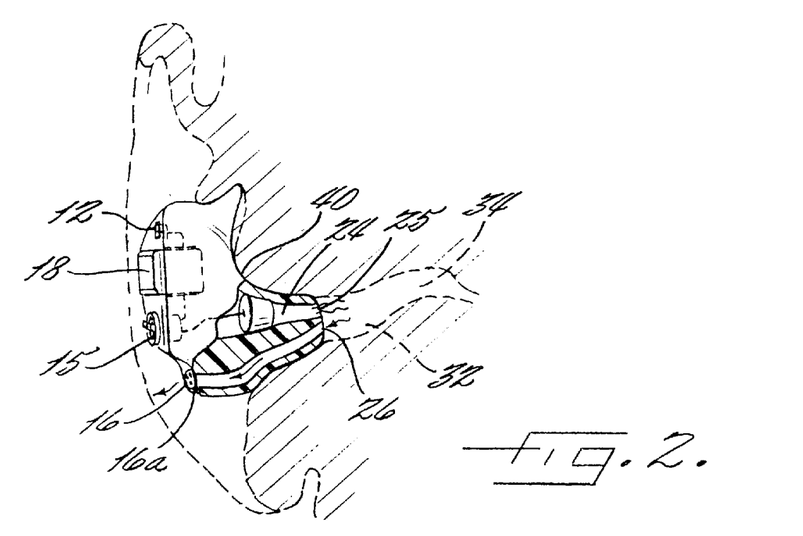
FIG. 2 is a cutaway sectional view of the device of FIG. 1, illustrating a device for ameliorating stuttering according to the present invention positioned in the ear canal.

Referring now to the drawings, one embodiment of a device to ameliorate stuttering is shown in FIG. 1. As illustrated, the device to ameliorate stuttering 10 is advantageously a single integrated unit which has a housing 30 configured to be received into the ear canal 32 close to the ear drum 34. Although shown throughout as a right ear model, a mirror image of the figure is applicable to the opposing, left ear. It is preferred that the housing 30 include a proximal portion which is insertable a predetermined distance into the ear canal 32 and is sized and configured to provide a comfortable, snug fit therein. The material of the housing 30 is preferably a hard or semiflexible polymer.

As shown in FIG. 1, a distal portion of the device 10 includes a receiver 12, a receiver inlet 13, an accessory access door 18, a volume control 15, and a small pressure equalization vent 16. The receiver 12, such as a transducer or microphone, is preferably disposed in a portion of the housing 30 which is positioned near the entrance to the ear canal 36 so as to receive sound waves with a minimum of blockage. It is more preferred that the receiver 12 be disposed on or adjacent a distal exterior surface of the housing and that the housing 30 optionally include perforations 13 to allow uninhibited penetration of the auditory sound waves into the receiver or microphone.

The device 10 also includes an accessory access panel, shown here as a door member 18. Advantageously, this member allows easy access to the device so as to enable the interchange of batteries, or to repair electronics, and the like. Further, this door member 18 can also act as an "on" and "off" switch. For example, the device can be turned on and off by opening and closing the door 18. The device further includes a volume control which is also disposed to be accessible by a patient. As shown the device includes raised gripping projectiles 15a for easier adjustment.

It is preferred that the proximal side of the device hold the transmitter or speaker 24. It is also preferred that the housing 30 be configured to generally fill the concha of the ear 40 to prevent or block undelayed signals from reaching the eardrum. As shown in FIG. 1, the proximal side of the housing 30 preferably includes at least two openings 25, 26. A first opening is a vent opening 26 in fluid communication with the pressure vent 16 on the opposing side of the housing 30. As such the vent openings 16, 26 can be employed to equalize ear canal and the ambient air pressure. The distal vent opening 16 can also be configured with additional pressure adjustment means to allow manipulation of the vent opening 16 to a larger size. For example, a removable insert 16a having a smaller external aperture can be configured to be received into a larger aperture in the vent. Thus, removal of the plug results in an "adjustable" larger pressure vent opening 16.

A second opening 25 disposed in the ear canal on the proximal side of the device is a sound bore 25 which delivers the processed signal to the inner ear canal. The opening preferably has no intermediate coverings permitting free, non-impeded delivery of the processed signal to the inner ear. Alternatively, thin membrane coverings or baffle coverings (not shown) may be employed over the sound bore 25 to protect the electronics from unnecessary exposure to biological contaminants.

If needed, the housing may contain a semi-flexible extension over the external wall of the ear (not shown) to further affix the housing 30 to the ear, or to provide additional structure and support, or to hold components associated with the device, such as power supply batteries. It is preferred that the electronic hardware components be powered by one or more batteries of suitable voltage.

Figure 3:
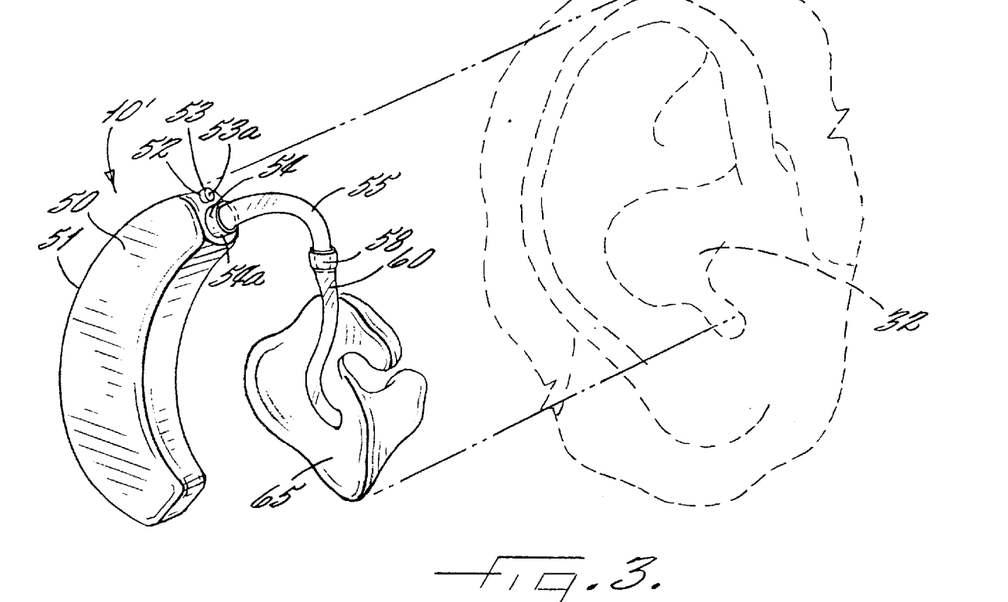
FIG. 3 is a side perspective view of an alternative embodiment of a behind-the-ear ("BTE") device for ameliorating stuttering according to the present invention.
Figure 4:
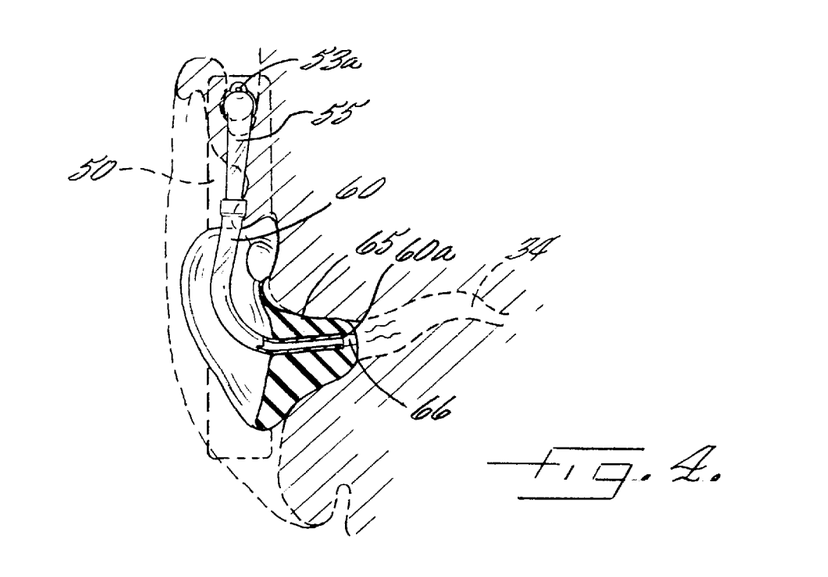
FIG. 4 is a partial sectional view of the device of FIG. 3, showing the device positioned behind the ear.

An alternative embodiment of a ameliorative stuttering device 10' is shown in FIGS. 3 and 4. This embodiment is a BTE device. As illustrated, the device 10' includes a standard hearing aid shell or housing 50, an ear hook 55, and an ear mold 65. The ear mold 65 is flexibly connected to the ear hook by mold tubing 60. The mold tubing 60 is sized to receive one end of the ear hook 58. The ear hook 55 is preferably formed of a stiffer material than the tubing 60. Accordingly one end of the ear hook 58 is inserted into the end of the mold tubing to attach the components theretogether. The opposing end of the ear hook 54 is attached to the housing 50. Preferably, the ear hook end 54 is threadably engaged with a superior or top portion of the housing 50.

As shown, the ear mold 65 is adapted for the right ear but can easily be configured for the left ear. The ear mold 65 is configured and sized to fit securely against and extend partially into the ear to structurally secure the device to the ear. Preferably, the tubing proximal end 60a extends a major distance into the ear mold 65, and more preferably extends to be slightly recessed or substantially flush with the proximal side of the ear mold 65. The tubing can direct the signal and minimize the degradation of the transmitted signal along the signal path in the ear mold.

The proximal side of the ear mold 65 includes a sound bore 66 in communication with the tubing 60. In operation, the signal is processed in the housing 50 and is transmitted through the ear hook 54 and tubing 60 into the ear mold 65 and is delivered to the ear canal through a sound bore 66.

An opening is formed in the housing 50 to receive the auditory signal generated by the patient's speech. Preferably, as illustrated in FIG. 3, the opening is in communication with an opening in a receiver such as a microphone 53 positioned on the housing. More preferably, the receiver or microphone 53 is positioned in an anterior-superior location relative to the wearer and extend out of the top of the housing 50 so as to freely intercept and receive the signals.

Preferably, corrosion resistant materials such as a gold collar or plating are included to surround the exposed component in order to protect it from environmental contaminants. It is also preferred that the microphone opening 53a be free of obstructions in order to allow the signal to enter freely therein.

Additionally, the housing 50 can employ various other externally accessible controls (not shown). For example the anterior portion of the housing 51 can be configured to include a volume control, an on-off switch, and a battery door. The door can also provide access to an internal tone control and various output controls. Optionally, the BTE device can include an external pack for carrying a battery pack and may include externally positioned signal processing circuitry. The external pack is connected to the housing (not shown) and configured to be light weight and portable, and preferably supportably attached to a user, via clothing, accessories, and the like.

In position, with the ear mold 65 in place, the BTE device is disposed with the ear hook 55 resting on the anterior aspect of the helix of the auricle with the body of the housing situated medial to the auricle adjacent to its attachment to the skull. Typically, the housing 50 is configured to follow the curve of the ear, i.e., is a generally elongated convex. The housing size can vary, but is preferably sized from about 1 inch to 2.5 inches in length, measured from the highest point to the lowest point on the housing. The ear hook 55 is generally sized to be about 0.75 to about 1 inch for adults, and about 0.35 to about 0.5 inches for children; the length is measured with the hook in the radially bent or "hook" configuration.

It is preferred that the receiver 12, 53, i.e., the microphone or transducer be positioned within a distance of about 1 cm. to 7 cm. from the external acoustic meatus of the ear. It is more preferable that the transducer be positioned within 4 cm of the external acoustic meatus of the ear and most preferable that the transducer be positioned within about 2.5 cm. It is noted that the embodiment illustrated in FIG. 1 is a single, integrated housing unit. Both the embodiments described can be conveniently and advantageously positioned adjacent the head. In particular, the device can be an ITE device positioned entirely within the concha of the ear and the ear canal ITE and a BTE device which is partially affixed over and around the outer wall of the ear so as to minimize the protrusion of the device beyond the normal extension of the helix of the ear, or as a CIC (not shown).

Hearing aids with circuitry to enhance hearing with a housing small enough to either fit within the ear canal or be entirely sustained by the ear are well known. For example, U.S. Pat. No. 5,133,016 to Clark, discloses a hearing aid with a housing containing a microphone, an amplification circuit, a speaker, and a power supply, that fits within the ear and ear canal. Likewise, U.S. Pat. No. 4,727,582 to de Vries et al., discloses a hearing aid with a housing having a microphone, an amplification circuit, a speaker, and a power supply, that is partially contained in the ear and the ear canal, and behind the ear. Each of the above-named patents are hereby incorporated by reference in their entirety as if fully recited herein.

As described above, the device to ameliorate stuttering is designed to be self-contained and portable. As such it does not require remotely located components. Although only two embodiments have been described, it will be appreciated by those of skill in the art that the invention is not limited thereto. Indeed, other configurations providing a portable and non-intrusive device which would allow for day-to-day use or "chronic" use would function in the manner intended by this device. Advantageously, this portable and economic unit allows for on-going use without remote loose hardware, i.e., the device employs a microphone which is affixed to the ear. This is especially important in devices directed to users who are young. Beneficially, enabling and allowing day to day use in early childhood may provide a higher cure rate, or at least partial reduction, of stuttering at an earlier age. Although described as a young childhood treatment, the device and method can also be practiced with adolescents and adults. Further, the device permits on-going therapy and feedback which is in complete contrast to conventional episodic type treatment (for example, therapy provided to a patient by a speech therapist with dedicated equipment at a clinic).

In order to provide on-going or chronic therapy, it is preferred that the chronic use device be worn for a predetermined block of time, i.e., for a minimum number of hours per day of use or per treatment day, and for a minimum number of treatment days within a treatment period (such as weekly, bimonthly, monthly or yearly). Thus, it is preferred that the be worn a minimum of 2, 3, 4, or 5 hours each treatment day and for majority of days within each treatment period. More preferably, the device is worn for a number of consecutive treatment days during each treatment period; for example, 3, 4, or 5 (e.g. consecutive days) days within a weekly treatment period, for 1, 2, or 3 or more consecutive weekly treatment periods. Further, the device can be effectively used in one, or both, ears. Indeed, at least some patients may benefit form the chronic use of the device in both ears (that is, two devices, one in each ear). See Andrew Stuart et al., *Effect of Monaural and Binaural Altered Auditory Feedback On Stuttering Frequency*, Jnl. Acous. Soc. Am. (July, 1997).

Figure 5:
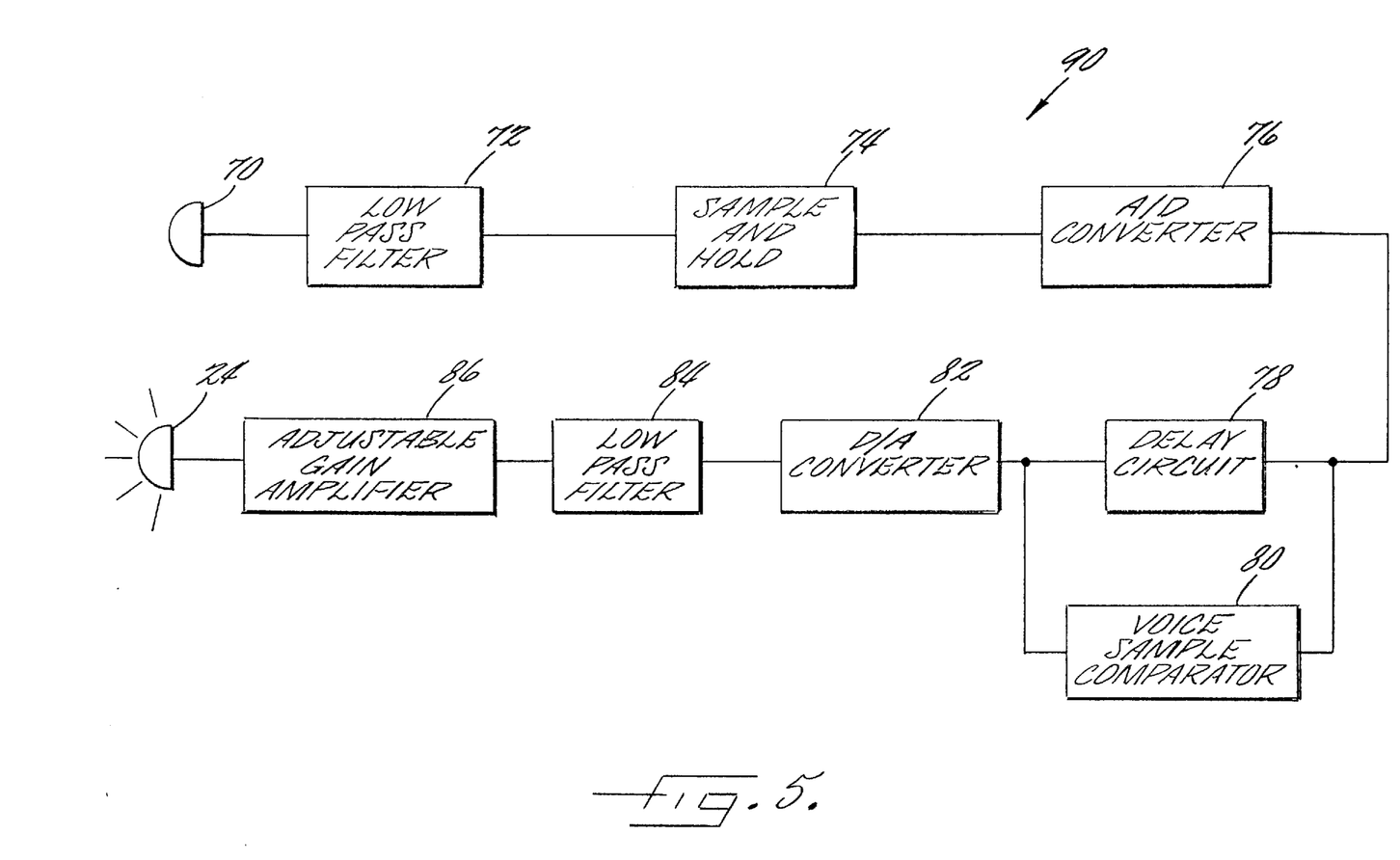
FIG. 5 is a schematic diagram illustrating the signal processing components for use with the device of the present invention.

The device can employ analog or digital signal processing ("DSP"). FIG. 5 illustrates a schematic diagram of an exemplary wave signal processor 90 (DSP) of a device to ameliorate stuttering. Generally described, the wave signal processor receives a signal generated by a user's speech; the signal is analyzed and delayed according to predetermined parameters. Finally, the signal is transmitted into the ear canal of the user.

As illustrated in FIG. 5, a receiver 70 such as a microphone or transducer 12 (53) receives the sound waves. The transducer 70 produces an analog input signal of sound corresponding to the user's speech. According to the embodiment shown in FIG. 5, the analog input signal is converted to a stream of digital input signals. Prior to conversion to a digital signal the analog input signal is filtered by a low pass filter 72 to prevent aliasing. The cutoff frequency for the low pass filter 72 should be sufficient to reproduce a recognizable voice sample after digitalization. A conventional cutoff frequency for voice is about 8 kHz. Filtering higher frequencies may also remove some unwanted background noise. The output of the low pass filter 72 is input to a sample and hold circuit 74. As is well known in the art the sampling rate should exceed twice the cutoff frequency of the low pass filter 72 to prevent sampling errors. The sampled signals output by the sample and hold circuit 74 are then input into an Analog-to-Digital (A/D) converter 76. The digital signal stream representing each sample is then fed into a delay circuit 78. The delay circuit 78 could be embodied in multiple ways as is known to one of ordinary skill in the art. For example, the delay circuit 78 can be implemented by a series of registers with appropriate timing input to achieve the delay desired.

Figure 6:
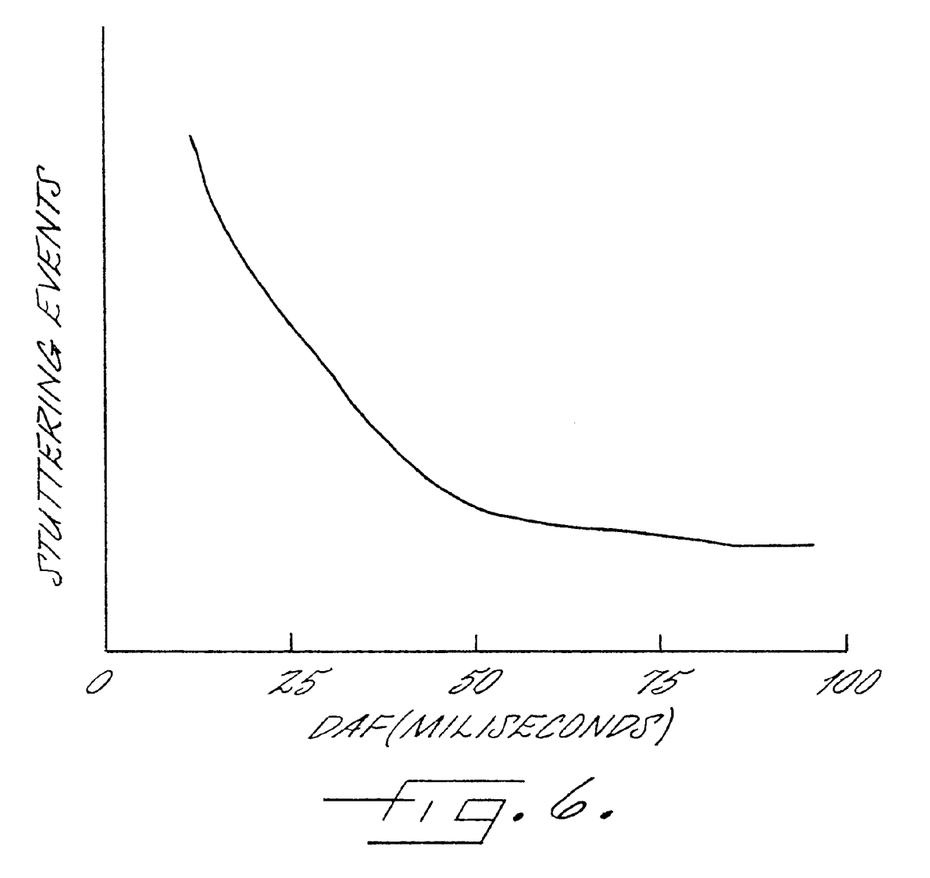
FIG. 6 is a graphical diagram illustrating numbers of stuttering events in relation to timing of the delayed auditory feedback.

As FIG. 6 illustrates, the number of stuttering events is significantly reduced when the speech is delayed. Therefore, it is preferred that the delay imposed on the digitized samples be set at above 10 ms, more preferably at above 25 ms, and still yet more preferably about or above 50 milliseconds. Generally, the delay will not be above 150 or 200 ms.

The auditory feedback signal can also be processed to include a frequency shift. The frequency shift will preferably be minimal so that the signal is less likely to be distorted, for example at about plus or minus 1/8, 1/2 or 1 octave shift. In one preferred embodiment, the altered auditory feedback will include a delay of about 50 ms and a frequency alteration at about plus/minus one-quarter or one-half of an octave. In terms of hertz, the frequency shift will be dependent upon the input signal. For example, for a 500 Hz input signal, a one octave shift is 1000 Hz; similarly, a one octave shift of a 1000 Hz input signal is 2000 Hz. In any event, it is preferred that the device be substantially "acoustically invisible" so as to provide the high fidelity of unaided listening and auditory self-monitoring while at the same time delivering optimal altered feedback, e.g, a device which reduces stuttering while maintaining a relatively normal speech pattern.

The output of the delay circuit (and optionally the frequency shift circuit) is then fed into a Digital-to-Analog (D/A) converter 82. The analog signal out of the D/A converter 82 is then passed through a low pass filter 84 to accurately reproduce the original signal. The output of the low pass filter 84 is fed into an adjustable gain amplifier 86 to allow the user to adjust the output volume of the device. Finally the amplified analog signal is connected to a speaker 24. The speaker 24 will then recreate the user's spoken words with a delay.

Optionally, the device for ameliorating stuttering may have an adjustable delay operatively associated with the auditory delay circuit. In such an embodiment, the delay circuit can include a detector which detects the number of stuttering events within a predetermined time envelope. The delay circuit or wave signal processor can include a voice sample comparator 80 for comparing a series of digitized voices samples input to the delay circuit 78, and output from the delay circuit 78. As is known in the art, digital streams can be compared utilizing a microprocessor. The voice sample comparator 80 will output a regulating signal to the delay circuit to increase or decrease the time delay depending on the number of stuttering events detected.

The device for ameliorating stuttering can also have a switching circuit (not shown) to interrupt transmission from the microphone to the earphone, i.e, an activation/deactivation circuit. An embodiment of this type of circuit is disclosed in U.S. Pat. No. 4,464,119 to Vildgrube et al., column 4, lines 40–59, incorporated herein by reference. The device for ameliorating speech can be interrupted either by manually switching power off from the batteries, or by automatic switching when the user's speech and corresponding signal input falls below a predetermined threshold level. This can prevent sounds other than the users speech from being transmitted by the device.

The use of DSP in ameliorative stuttering devices can have increased power requirements and may require a portable external battery pack and or an external processing unit or components thereof. Such an external battery pack may conveniently be configured to attach to belts, clothing and the like. An example of a known BTE hearing aid including digital signal processing worn with an external battery and processing pack, the PHOENIX™, has been produced by the NICOLET Company of Madison, Wis.

Alternatively, as is known in the art an equivalent delay circuit can be obtained with an analog delay circuit such as a bucket-brigade circuit. Alternatively, as is also known in the art, other circuit components can be interchanged with those described above and would perform according to the present invention.

Also, as will be appreciated by those of skill in the art, the wave signal processor and other electronic components as described above may be provided by hardware, software, or a combination of the above. Thus while the various components have been described as discrete elements, they may in practice be implemented by a microcontroller including input and output ports running software code, by custom or hybrid chips, by discrete components or by a combination of the above. For example, one or more of the A/D converter 76, the delay circuit 78, the voice sample comparator 80, and the gain 86 can be implemented as a programmable controller device. Of course, the discrete circuit components can also be mounted separately or integrated into a printed circuit board. See generally Wayne J. Staab, *Digital Hearing Instruments*, 38 Hearing Instruments No. 11, pp. 18–26 (1987).

As described above, the altered feedback circuit may be analog or digital. As is well known to those of skill in the art, an analog device generally requires less power than a device which includes DSP and as such can be lighter weight and easier to wear than a DSP unit. Also known to those of skill in the art, analog units are generally less suitable for manipulating a frequency shift into the received signal due to non-desirable signal distortions typically introduced therewith. Advantageously, DSP units can be used to introduce one or more of a time delay and a frequency shift into the feedback signal. FAF used with DAF can provide increased effectiveness in stuttering treatment in some individuals. See J. MacLeod et al., *Effect of Single and Combined Altered Auditory Feedback On Stuttering Frequency at Two Speech Rates*, 28 Journal of Communication Disorders, p. 217–228 (1995).

In any event, the electroacoustic operating parameters of the device preferably include individually adjustable and controllable power output, gain, and frequency response components. Of course, fixed circuits can also be employed with fixed maximum output, gain, and frequency response while also providing an adjustable volume control for the wearer. In operation, the ameliorative stuttering device will preferably operate with "low" maximum power output, "mild" gain, and a relatively "wide" and "flat" frequency response. More specifically, in terms of the American National Standards Institute Specification of Hearing Aid Characteristics (ANSI S3.22-1996), the device preferably has a peak saturated sound pressure level-90 ("SSPL90") equal to or below 110 decibels ("dB") and a high frequency average (HFA) SSPL90 will preferably not exceed 105 dB. Preferably, a peak gain will not exceed 50 dB and a HFA full on gain will not exceed 45 dB. A frequency response is preferably at least 200–4000 Hz, and more preferably about 200–8000 Hz. It is preferred that the frequency response be "flat" with some compensatory gain between about 1000–4000 Hz. For example, about 10–20 dB between 1000–4000 Hz to accommodate for the loss of natural external ear resonance. This natural ear resonance is generally attributable to the occluding in the external auditory meatus and or concha when a CIC, ITE or ear mold from a BTE stuttering device is employed. It is also preferred that the harmonic distortion be less than 10% and an equivalent input noise is less than 35 dB.

Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents by also equivalent structures. The invention is defined by the following claims, with equivalents of the claims to be included therein.

That which is claimed is:

1. A device for ameliorating stuttering supported by the ear of an individual, said device comprising:
   (a) a housing having opposing distal and proximal surfaces, wherein at least said proximal surface configured for positioning within the ear canal of said individual;
   (b) a wave signal processor contained within said housing, said wave signal processor comprising:
      (i) a receiver, said receiver generating an input signal responsive to an auditory signal associated with said individual's speech;
      (ii) a delayed auditory feedback circuit operably associated with said receiver for generating a delayed auditory signal; and
      (iii) a transmitter contained within said housing and operably associated with said delayed auditory feedback circuit for transmitting a delayed auditory signal to said individual; and
   (c) a power source operatively associated with said wave signal processor for supplying power thereto.

2. A device according to claim 1, wherein said device is an ITE device.

3. A device according to claim 1, wherein said device is a CIC device.

4. A device according to claim 1, wherein said receiver is positioned within a distance of about 1 cm. to 7 cm. from the external acoustic meatus of the ear.

5. A device according to claim 4, wherein said receiver is a microphone, and wherein said microphone is positioned on the distal surface of said housing.

6. A device according to claim 5, wherein said microphone is positioned within about 4 cm from the acoustic meatus of said individual.

7. A device according to claim 1, further comprising adjustable gain, power, and frequency response components operably associated with said wave signal processor and disposed in said housing.

8. A device according to claim 1, wherein said delayed auditory feedback circuit provides a delay of about at least 25 milliseconds.

9. A device according to claim 8, wherein said device shifts the frequency of said delayed feedback signal between about plus one-half octave to about minus one-half octave.

10. A device according to claim 8, further comprising:
   an activation circuit responsive to an auditory signal for activating said signal processor to an operative condition and deactivating said signal processor to a nonoperative condition responsive to an absence of an auditory signal.

11. A device according to claim 8, further comprising:
a detetctor operably associated with said receiver for detecting at least one stuttering event.

12. A device according to claim 1, wherein said wave signal processor is configured to shift the frequency of said auditory input signal.

13. A device according to claim 1, wherein said delayed auditory feedback circuit includes an adjustable delay for adjusting the delay provided by said delayed auditory feedback circuit, said adjustable delay configured so that increased time delays are provided for increasing numbers of detected stuttering events.

14. A device according to claim 1, wherein said device has a peak saturated sound pressure level-90 (SSPL90) equal to or below 110 decibels.

15. A device according to claim 14, wherein said device has a high frequency average (HFA) SSPL90 less than about 105 dB.

16. A device according to claim 15, wherein said device has a HFA full on gain less than about 45 dB.

17. A device according to claim 1, wherein said device has a peak gain less than about 50 dB.

18. A device according to claim 1, wherein said device has a frequency response in the range of about 200–4000 Hz.

19. A device according to claim 18, wherein the frequency response is substantially flat.

20. A device according to claim 1, wherein said device has a frequency response in the range of about 200–8000 Hz.

21. A device according to claim 1, wherein said device includes compensatory gain between about 1000–4000 Hz thereby compensating for the loss of natural external ear resonance introduced by said device.

22. A device according to claim 21, wherein said compensatory gain is in the range of about 10–20 dB.

23. A device according to claim 1, wherein said device is devoid of remotely positioned transducer and tactile apparatus.

24. A device according to claim 1, wherein said device includes two separate housings configured to provide binaural altered auditory feedback, and wherein one proximal surface of each of said housings is configured to be positioned in a different ear of an individual.

25. A device for ameliorating stuttering positioned BTE of an individual, said device comprising:
(a) an ear mold having a portion adapted to be received into the ear of said individual;
(b) a housing in communication with said ear mold configured for positioning behind the ear of said individual;
(c) a receiver positioned adjacent said housing, said receiver generating an input signal responsive to an auditory signal associated with speech of said individual;
(d) a delayed auditory feedback circuit disposed in said housing and operatively associated with said receiver for generating a delayed auditory signal;
(e) a transmitter operably associated with said delayed auditory feedback circuit for transmitting the delayed auditory signal to the individual; and
(f) a power source operatively associated with said receiver, said delayed auditory feedback circuit, and said transmitter for supplying power thereto.

26. A device according to claim 25, wherein said receiver is positioned within a distance of about 1 centimeter to 7 centimeters from the external acoustic meatus of the ear.

27. A device according to claim 25, further comprising adjustable gain, power, and frequency response components operably associated with said delayed auditory feedback circuit and disposed in said housing.

28. A device according to claim 25, wherein said delayed auditory feedback circuit provides a delay of about at least 25 milliseconds.

29. A device according to claim 25, wherein said delayed auditory feedback circuit includes an adjustable delay for adjusting the delay provided by said delayed auditory feedback circuit, said adjustable delay configured so that increased time delays are provided for increasing numbers of detected stuttering events.

30. A device according to claim 25, further comprising:
an activation circuit responsive to an auditory signal for activating said signal processor to an operative condition and deactivating said signal processor to a non-operative condition responsive to an absence of an auditory signal.

31. A device according to claim 30, further comprising:
a detector operably associated with said receiver for detecting at least one stuttering event.

32. A device according to claim 25, wherein said receiver is a microphone, and wherein said microphone is disposed on the top of the housing such that when worn it is positioned in an anterior-superior location relative to the wearer's ear so as to freely intercept and receive the user's auditory signals.

33. A device according to claim 25, wherein properly positioned on said individual said microphone is positioned within about 4 cm from the acoustic meatus of said individual.

34. A device according to claim 25, wherein said device has a peak saturated sound pressure level-90 (SSPL90) equal to or below 110 decibels.

35. A device according to claim 25, wherein said device has a high frequency average (HFA) SSPL90 less than about 105 dB.

36. A device according to claim 35, wherein said device has a HFA full on gain less than about 45 dB.

37. A device according to claim 25, wherein said device has a peak gain less than about 50 dB.

38. A device according to claim 25, wherein said device has a frequency response in the range of about 200–4000 Hz.

39. A device according to claim 25, wherein said device has a frequency response in the range of about 200–8000 Hz.

40. A device according to claim 39, wherein the frequency response is substantially flat.

41. A device according to claim 40, wherein said device includes compensatory gain between about 1000–4000 Hz thereby compensating for the loss of natural external ear resonance introduced by said device.

42. A device according to claim 41, wherein said compensatory gain is in the range of about 10–20 dB.

43. A device according to claim 25, wherein said device is configured to shift the frequency of said feedback signal.

44. A device according to claim 43, wherein said frequency shift is between about plus one-half octave to minus one-half octave.

45. A device according to claim 25, wherein said device includes two separate housings configured to provide binaural altered auditory feedback, and wherein one proximal surface of each of said housings is configured to be positioned in a different ear of an individual.

46. A method for chronic amelioration of stuttering, comprising the steps of:
(a) positioning a self-contained ameliorative stuttering device for receiving auditory signals associated with an individual's speech in close proximity to the ear of an individual, the device being adapted to be in communication with the ear canal of said individual;

(b) receiving an audio signal associated with said individual's speech;

(c) generating a delayed auditory signal responsive to the received audio signal;

(d) transmitting the delayed auditory signal to the ear canal of the individual.

47. The method according to claim 46, wherein said delayed auditory signal is delayed at least 25 milliseconds.

48. The method according to claim 46, further comprising the step of comparing a series of digitized voices samples input to the delay circuit with the output from the delay circuit to determine if the timing of the output auditory delay signal is sufficient.

49. The method according to claim 44, further comprising the step of adjusting the delay of said delayed auditory signal delay responsive to the determination of said comparing step, thereby increasing or decreasing the time delay output from said delay circuit corresponding to the number of stuttering events detected.

50. The method according to claim 46, wherein said stuttering device is worn a minimum of 3 hours during each day of use.

51. The method according to claim 50, wherein said stuttering device is worn a majority of days within each treatment period.

52. The method according to claim 51, wherein said stuttering device is worn a consecutive number of days within each treatment period.

53. The method according to claim 46, wherein said stuttering device is worn in both ears.

54. The method according to claim 46, further comprising the step of generating a frequency shift in said time delayed feedback signal prior to step (d).

* * * * *

UNITED STATES PATENT AND TRADEMARK OFFICE
CERTIFICATE OF CORRECTION

PATENT NO. : 5,961,443
DATED : October 5, 1999
INVENTOR(S) : Michael Pierre Rastatter; Joseph Stanley Kalinowski; Andrew Michael Stuart

It is certified that error appears in the above-identified patent and that said Letters Patent is hereby corrected as shown below:

Under paragraph entitled "References Cited" correct 4,464,419 to read --4,464,119--.

Column 13, Claim 49, Line 16, correct "claim 44" to read --claim 48--.

Signed and Sealed this

First Day of May, 2001

Attest:

NICHOLAS P. GODICI

*Attesting Officer*     *Acting Director of the United States Patent and Trademark Office*